(12) United States Patent
Rabiner et al.

(10) Patent No.: US 6,579,277 B1
(45) Date of Patent: Jun. 17, 2003

(54) VARIABLE STIFFNESS MEDICAL DEVICE

(75) Inventors: Robert A. Rabiner, North Reading, MA (US); Daniel E. Rabiner, North Reading, MA (US)

(73) Assignee: OmniSonics Medical Technologies, Inc., Wilington, MA (US)

( * ) Notice: Subject to any disclaimer, the term of this patent is extended or adjusted under 35 U.S.C. 154(b) by 75 days.

(21) Appl. No.: 09/663,017

(22) Filed: Sep. 15, 2000

Related U.S. Application Data

(60) Provisional application No. 60/156,053, filed on Sep. 24, 1999.

(51) Int. Cl.$^7$ .............................................. A61M 25/00
(52) U.S. Cl. ........................................ 604/525; 604/22
(58) Field of Search ........................ 604/93.01, 164.01, 604/164.07, 164.11, 166.01, 523, 524, 525, 526, 164.1, 264, 167.09, 22; 606/127, 128

(56) References Cited

U.S. PATENT DOCUMENTS

| | | |
|---|---|---|
| 4,738,666 A | 4/1988 | Fuqua |
| 5,123,903 A | 6/1992 | Quaid et al. |
| 5,897,569 A | 4/1999 | Kellogg et al. |
| 6,156,018 A * | 12/2000 | Hassett ....................... 600/585 |

* cited by examiner

Primary Examiner—Manuel Mendez
Assistant Examiner—Mark K. Han
(74) Attorney, Agent, or Firm—Palmer & Dodge, LLP; Richard B. Smith

(57) ABSTRACT

A medical device such as an endoscope has an elongated flexible sheath. A first sleeve has a passage there through which snugly receives the sheath, the first sheath being slide-able from its proximal end to its distal end. The sleeve is a thin-walled tube having a constant inner diameter so as to minimize the increase the outer dimension of the device at the portion upon which the sleeve is positioned. The sleeve has a length of approximately one-half the length of the sheath and may have greater stiffness than the sheath. A second sleeve may be slide-ably mounted on the first sleeve and has a snug fit therewith. The second sleeve is also a thin-walled tube having a constant outer dimension. The second sleeve has a length of approximately one-half the length of the first sleeve and may have greater stiffness than the first sleeve.

18 Claims, 2 Drawing Sheets

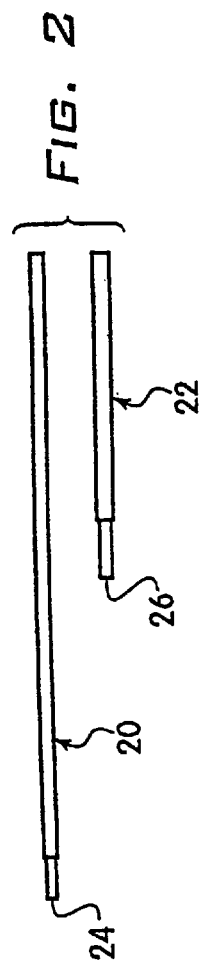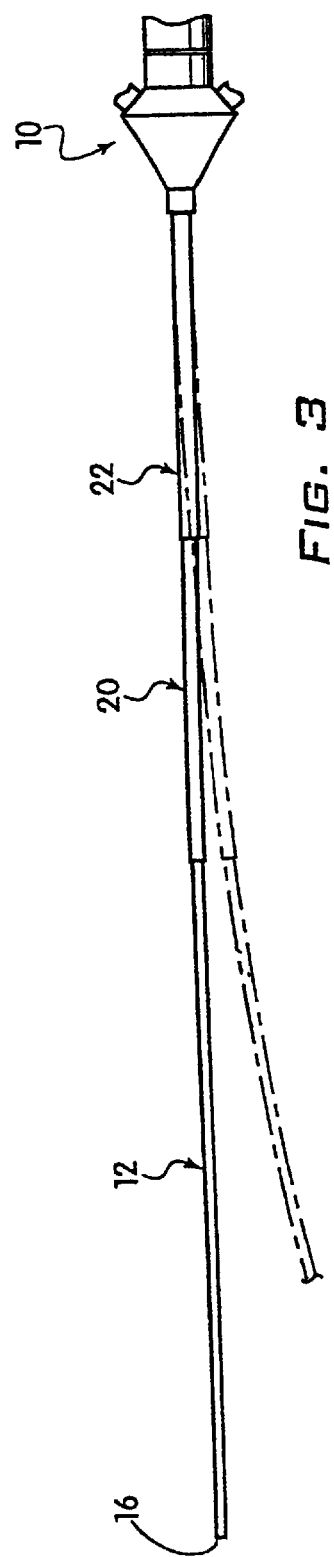

VARIABLE STIFFNESS MEDICAL DEVICE

This application claims the benefit of Provisional application Ser. No. 60/156,053, filed Sep. 24, 1999.

BACKGROUND OF THE INVENTION

1. Field of the Invention

The present invention relates to medical devices such as small diameter endoscopes, catheters, probes and/or other semi-rigid, semi-flexible instruments having an elongated insertion tube which is flexible, and more particularly to such devices which incorporate mechanisms for varying the stiffness of the device.

2. Description of Related Art

It is usually necessary to provide some amount of initial rigidity/columnar strength upon the initial insertion of a device (such as endoscopes, catheter devices, or probes) in order for the device to pass through natural or manmade orifices and passages without bending or buckling and enter the human body. Unfortunately, the initial rigidity of a device is usually too stiff to allow for and provide for residual flexibility within the human body, which includes many changes in direction.

The residual flexibility is necessary to ensure that the device does not puncture organs or vessels, and ensure that the device is able to follow the anatomical passages without causing injury to the passage. Furthermore, the introduction of flexibility to a given probe enables the device to accommodate small amounts of compression, so as to traverse bends in the anatomy, without inducing torsional/tearing forces on the tissue. For example, driving a straight, relatively stiff rod thought a tortuous vessel will induce tearing stresses on the vessel where the vessel has a large degree of directional change.

The present invention is particularly well suited for use with an ultrasonic probe operating in a transverse mode of operation, as described in our co-pending application Ser. No. 09/618,352, which was filed on Jul. 19, 2000 and is herein incorporated by reference in its entirety. In prior art devices, the application of ultrasonic energy has required that the inserted probe be relatively rigid. These relatively rigid probes were required to transmit ultrasonic energy, and limited the flexibility of the ultrasonic probe. Through the application of transverse ultrasonic energy, flexible ultrasonic probes are able to be produced. The present invention is particularly well-suited for use with these probes.

Prior art medical devices currently available are usually either too flexible or too stiff to easily manipulate within the human body and provide the aforementioned needs and issues. In the construction of prior art medical devices, the flexibility has been predetermined at the time of construction. The flexibility cannot be adjusted to suit specific anatomical or user conditions encountered in various medical procedures. This predetermined flexibility is based upon the diameter, wall thickness and durometer of the material used. Alternatively, where allowable, intricate steering and stiffening devices have been added to the instrument to influence the predetermined flexibility. Some examples of these steering/stiffening devices are wires embedded within a catheter tube that allow for directional changes to be caused by pulling/easing of the wires, and then to stiffen the device by applying equal retraction on the wires so as to cause compression on the column and inducing stiffness to it.

Furthermore, prior to the present invention the length of the flexible portion of the device—along with the strength modulus of the materials used in the probe construction determined the overall compression/deflection factor on the probe and the subsequent ability of the device to bow and bend and particularly how much prior to eventual breakage.

With reasons and necessity for a wider degree of flexibility within use in the human anatomy, it is desirable to provide a medical device wherein the stiffness thereof can be varied through a relatively wide range with a relatively simple and inexpensive construction.

SUMMARY OF THE INVENTION

Accordingly, an object of the invention is to provide a medical device with variable stiffness, so that the device provides sufficient initial rigidity to allow initial insertion into a body, yet provides sufficient residual flexibility to allow manipulation within the human body. An object of the invention is to provide a single-use product. In this aspect of the invention, the method of construction and design has been directed towards those products which are considered to be single patient contact. This provides a device which does not require complicated methods of disassembly and cleaning procedures and processes prior to reuse of the device.

Another abject of the present invention is to provide a design with minimal incremental cost increases when compared to existing devices. This is important factor because of financial constraints placed upon the medical markets and healthcare reimbursement.

A further object of the invention is to eliminate the use and introduction of wires and or other devices within the lumen of the probe (if hollow) and eliminate any fixation or similar attachments to the exterior of the probe.

Another object of the invention is to minimize the size of the medical device. It is known that any increase in outer dimension significantly increases the circumference and hence contact with the human anatomy. Similarly, the portion of the medical device which penetrates the human body should be minimized to ensure that the device is (where appropriate) more comfortable, less traumatic and easily tolerated by a patient and/or fits within the confines of existing medical instrumentation.

For example, when inserting diagnostic instrumentation into the cervix of a human uterus, the smallest outer dimension is desired in order to preclude the need for cervical dilation. Unfortunately, the small diameter devices required for such procedures must be relatively flexible so as to preclude accidental puncture of the organ, as well as to be able to be deflected so as to reach anatomical landmarks. However this flexibility increases the degree of difficulty of insertion of the device, as well as subsequent manipulation. Thus, increasing the durometer, increasing wall stiffness and or diameter—with a result in the decrease in flexibility may assist in the introduction of the probe, but can cause a risk of damage.

Yet another object of the invention is to provide the ability to provide modification to the location of the maximum point of flexure along the probe. By having the ability to move or altering the location of the flexure point, the probe is able to maximize its utility within the human anatomy.

Another object of the present invention is to provide a device capable of the delivery of an active ultrasonic probe—where the thinner/softer wires are required for the effective positioning and delivery into the human anatomy. As the wires of an ultrasonic probe are made thinner and softer, the transmission of the ultrasonic energy may be reduced. The probe may, over the length of the active portion, start to exhibit undesired flexural modes or, may incur losses due to contact with soft acoustically absorbing materials.

A further object of the present invention is to provide the ability to modify the stiffness of an ultrasonic probe so as to allow for the insertion/manipulation of that probe within the confines of the human anatomy—while at the same time not reducing the stiffness such that it cannot/will not provide sufficient power to destroy tissue.

In accordance with these objects, a medical device such as an endoscope, catheter, or ultrasonic probe includes an insertion tube or trocar, which is adapted to penetrate into the human body. A trocar is a surgical instrument that contains two parts: a trocar sheath and an obturator. The trocar sheath is an outer thin walled tube that surrounds the obturator. The obturator contains a point or sharpened profile that is able to penetrate the human anatomy.

For convenience, the present invention is described in conjunction with trocars. However, trocars are merely used for illustration, and one skilled in the art will recognize that any alternative vascular access devices and instruments for percutaneous introduction and access to the vasculature can be utilized as well, and that the current invention is capable of application and utility to a wide variety of surgical procedures.

Once the trocar has been inserted within the organ or body, the obturator is removed and the instrument to be inserted into the anatomy is slid within the confines of the trocar inner walls—and passed forward. In traditional instruments, at this point the predetermined flexibility (or lack thereof) defines the use and utilization of the device.

In the present invention, a tube or sleeve is designed to be received within the trocar sleeve. The sleeve is sized so that it fits over the outer diameter of the inserted flexible probe. The sleeve (or series of sleeves) are comprised of a thin walled tube(s) having a substantially constant diameter. The edges of the tubes are radiused or champhered so that they do not introduce sharp edges or obstruction points to tissue or surrounding materials as they are engaged and moved. The tube(s) can be constructed of any materials suitable to form a thin-walled structure, such as polyamide, Teflon, or other polymers and materials. Preferably, the materials have sufficient stiffness to maintain their own respective column and are able to increase the flexural rigidity of the probe to which they have been applied to.

The sleeve that is applied to the outer diameter of the probe may be tapered from one end to that of its maximum diameter, such that it provides a taper that is capable of functioning as the trocar sleeve with the inner probe functioning somewhat as the obturator—in this manner the series of sleeves would cause—when in proper orientation, a continual taper from the beginning of the shaft of sleeves to the end.

A variation of the system would be that where a series of these outer tubes, and the tapers are able to be mated and joined such that the sum of the diameters and the tapers, produces a relatively more significant diameter and taper.

Irrespective of outer dimensional shapes, the stiffening sleeve is designed to be placed around the outer diameter of the flexible portion of the probe. The sleeve can then be advanced in a sliding fashion along the length of the flexible probe.

The stiffening sleeve receives the inner flexible probe, which is slide-able along the inner diameter of this tube. By advancing and/or moving the relationship of the outer stiffening sleeve to that of the inner probe, and by appropriate placement of the stiffening sleeve to that of the flexible column, the stiffness of the device may be varied through a wide range.

The length of the sleeve is approximately one-half the length of the flexible portion of the medical device. The device can be configured with peel-away or removable segments, so that the length at the time of use may be varied. As the sleeve is moved from the proximal end of the flexible portion toward the distal end thereof, the sleeve stiffens the flexible portion, increasing the column strength of the flexible portion. This prevents bowing and makers it easier to insert the flexible portion into the human body.

If the sleeve is stiffer than the insertion tube of the medical device, the compression factor of the flexible portion is thereby modified to suit specific surgical needs and conditions of the patient.

The use of a thin-walled sleeve of substantially constant outer dimension or tapered as previously mentioned minimizes the increase in outer dimension of the device in the area where the sleeve is positioned. However, a variable taper in the sleeve can also be provided, where the thickest portion of the wall is in the area of maximum force application. This is generally the area near the insertion point, where the loads are maximum, and thereafter the outer dimension of the sheath may be reduced.

A second sleeve may be slide-ably mounted on the first sleeve and snugly receives the first sleeve. The second sleeve has a length of about one-half the length of the first sleeve and further may have stiffness greater than that of the first sleeve. The second sleeve is slideable along the entire length of the first sleeve and thereby provides a means for further adjusting the stiffness of the medical device. The two sleeves may be independently adjusted relative to one another whereby the stiffness of the device can be adjusted in relatively small increments of stiffness.

Since both of the sleeves are thin-walled tubes with constant outer dimensions, the increase in outer dimension of the device when two sleeves are employed is minimal.

The first sleeve may be normally positioned on the insertion tube at the proximal end thereof. When it is desired to conduct a medical procedure within a human uterus, the sleeve surrounding the tube may be slid from the proximal end of the tube to a position near the distal end of the tube, whereupon the distal end of the tube is inserted into the cervical canal. The sleeve provides the requisite column strength to the device preventing bending of the tube upon insertion at maximum force or load, but, once withdrawn, allowing the tube to follow the anatomical curves of the cervix. The device permits the use of smaller medical devices, which are less invasive, while being more comfortable, less traumatic and more easily tolerated.

Additionally, the device could be made as an attachment piece that gets added to flexible products. For example, the device could be made of a shrink tube-type material that has a lubricant coating on the interior. The tube is applied to the flexible device and shrunk onto the flexible device using heat or a hot air gun. The tube would shrink to fit the flexible device, yet still be slide-able enough to still move. As a result, custom-fit products could be manufactured.

As the tube that is placed over the inner tube to induce stiffness, it may be conceived as a means and method to merely reduce the length of the flexible portion of the probe thereby inducing column stiffness.

As shown in FIG. 4, in the use with ultrasonic probes, especially those working in the transverse mode— significantly tight tubes circumferential to the probe may have a tendency to dampen the ultrasonic vibration of the probe, as the forces and, amplitude of the probe are transferred to the tube. In a preferred embodiment of the interior of the tube 20, internal ridges 55 are introduced (spaced in accordance with the nodal 53 and anti-nodal 51 spacing in accord with the frequency of the probe). As a result of these internal notches 55/spacing—while columnar contact and rigidity is maintained by the use of the external tube 20—the internal contact is minimized and does not result in losses to the probe.

The slideable members may also be devised such that they are not uniform in structural rigidity—i.e. the tubes do not need to be uniform in their inherent rigidity. Rather than the tubes being concentric (circular) the tube might be softer in one side of the tube and stiffer on the other. In this fashion, the ability to adjust the deflection and rigidity of the product is affected not only by the forward motion of the sliding sheath, but also by the orientation of the tube as it relates to the inner tube. By moving the outer sheath forward & backward as well as twisting the probe to direct the stiffness of the tube—increased decreased stiffness can be modified with greater precision.

BRIEF DESCRIPTION OF THE DRAWINGS

FIG. 1 is an elevation of a conventional endoscope;

FIG. 2 is an exploded view showing a pair of sleeves for use with the endoscope shown in FIG. 1; and FIG. 3 is an elevation showing the sleeves of FIG. 2 mounted in operative position on the endoscope.

DESCRIPTION OF THE PREFERRED EMBODIMENTS

Figure 4:
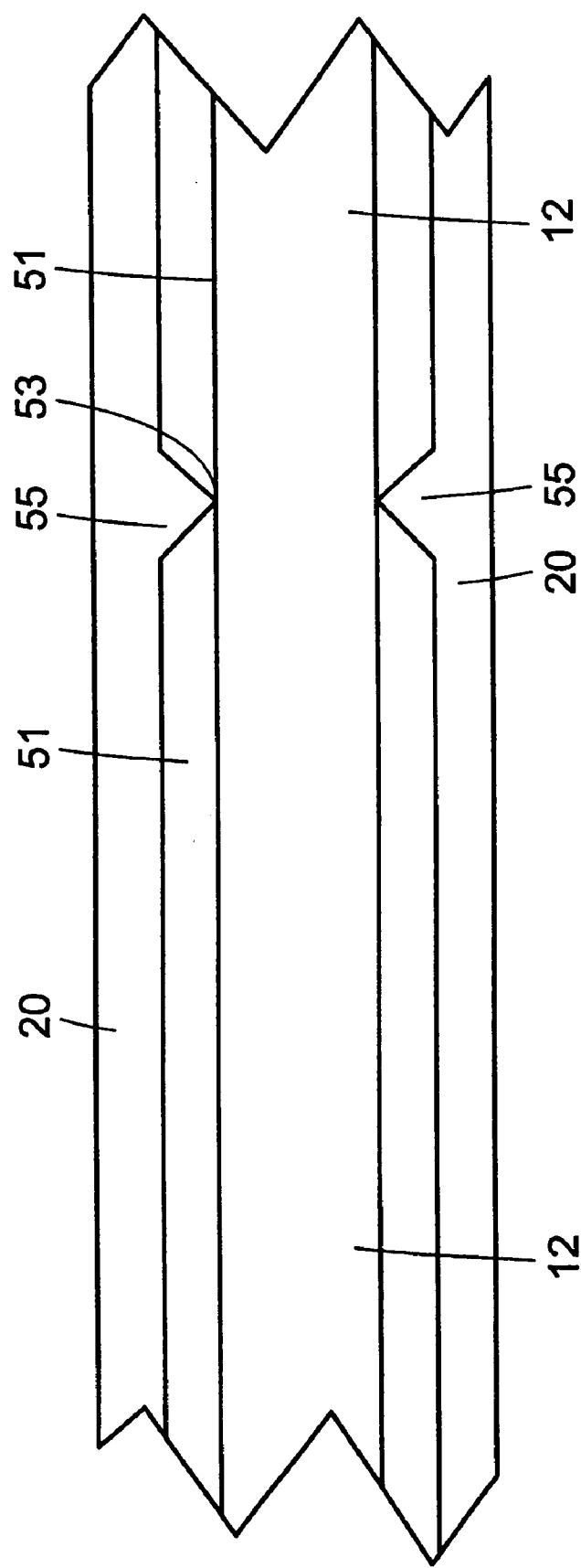
FIG. 4 is a fragmentary cross sectional view of a portion of FIG. 3.

Referring now to the drawings wherein like reference characters designate corresponding parts throughout the several views, there is shown in FIG. 1 a conventional endoscope including a conventional body 10 having a flexible insertion tube 12 of circular cross section extending there from and containing the usual channels and optical fibers therein. The insertion tube includes a proximal and 14 and a distal end 16.

The solid line position shown in FIG. 1 illustrates the normal orientation of the insertion tube 12 with respect to the body 10. The dotted line position shown in FIG. 1 illustrates the manner in which the tube is adapted to bend when it is inserted into the human body. The tube may be formed of a curable organic polymer such as polyamide.

Referring to FIG. 2, a first thin-walled sleeve 20 and second thin-walled sleeve 22 of substantially constant outer diameter and having circular cross sections are provided for varying the stiffness of the device. The first and second sleeves may be formed of the same material as the insertion tube, or they may be formed of a material having greater stiffness than the tube if desired. Only the first sleeve 20 may be used in combination with the insertion tube 12, or both sleeves may be employed as explained below.

The first sleeve 20 has a passage 24 formed there through of circular cross-section the diameter of which is such that the first sleeve 20 can be mounted on the outer surface of the insertion tube 12 so that the outer surface of the tube is snugly received within the passage 24, but the sleeve is adapted to slide along the tube. Only the first sleeve 20 may be mounted on the insertion tube 12 to vary the stiffness of the device, or both the first and second sleeves 20 and 22 may be mounted on the tube to provide a finer adjustment of stiffness if so desired.

The second sleeve 22 has a passage 26 formed there through of circular cross-section. The diameter of the passage 26 is such that the second sleeve 22 can be mounted on the first sleeve 20 so that the outer surface of the first sleeve 20 is snugly received within the passage 26 in the second sleeve, but the second sleeve 22 is adapted to slide along the first sleeve 20.

Referring to FIG. 3, the first sleeve 20 is shown in operative position surrounding the insertion tube 12; and the second sleeve 22 is shown in operative position surrounding the first sleeve 20. The length of the first sleeve 20 is approximately one-half the length of the insertion tube 12, while the length of the second sleeve 22 is approximately one-half the length of the first sleeve 20.

The first sleeve 20 is slide-able over the entire distance between the proximal and distal portions of the insertion tube 12. The second sleeve 22 is slide-able over the entire length of the first sleeve 20. The two sleeves may be independently adjusted relative to one another so that the stiffness of the device can be adjusted over a wide range in relatively small increments of stiffness.

As seen in FIG. 3, the first and second sleeves 20 and 22 have been moved to the right as far as they will go, and the addition of the two sleeves has reduced the flexibility of the insertion tube 12 as indicated by the broken lines. It is apparent that by sliding the first and second sleeves 20 and 22 to the left as seen in FIG. 3 toward the distal end 16 of the tube, the stiffness of the device may be increased, particularly at the distal end of the insertion tube.

The invention has been described with reference to a preferred embodiment. Obviously, various modifications, alterations and other embodiments will occur to others upon reading and understanding this specification. It is our intention on to include all such modifications, alterations come within the scope thereof. Any modifications or variations which fall within the purview of this description are intended to be included as part of the invention. It is understood that the description herein is intended to be illustrative only and is not intended to be limitative. Rather, the scope of the invention described herein is limited only by the claims.

What is claimed is:

1. A variable stiffness medical device comprising,
    an ultrasonic medical device including an elongated flexible ultrasonic probe operating in a transverse mode having a length and an outer surface defining an outer dimension to support a transverse ultrasonic vibration along a portion of the length of the elongated flexible ultrasonic probe,
    a sleeve having a passage there through, said elongated flexible ultrasonic probe extending through said passage with said outer surface of said elongated flexible ultrasonic probe being engaged by said passage, said sleeve being slide-able along said elongated flexible ultrasonic probe, said sleeve comprising a thin-walled tube having a substantially constant outer dimension so as to minimize the increase in outer dimension of the elongated flexible ultrasonic probeat the portion thereof upon which the sleeve is positioned,
    wherein the variable stiffness medical device provides sufficient residual flexibility to allow for manipulation within an anatomical passage in a human body.

2. A device as defined in claim 1, wherein said sleeve has a length which is approximately the length of said elongated flexible ultrasonic probe.

3. A device as defined in claim 1, wherein said sleeve is formed of a flexible material.

4. A device as defined in claim 1, wherein the sleeve is formed of a material having a stiffness to maintain its own column.

5. A device as defined in claim 1, wherein the combination of increased outer diameters increases the rigidity of the inner materials.

6. A device as defined in claim 1, wherein the location of the flexure of the elongated flexible ultrasonic probe can be adjusted.

7. A device as defined in claim 1, wherein the distal end of the elongated flexible ultrasonic probe is supported less than the proximal end of the elongated flexible ultrasonic probe.

8. A device as defined in claim 1, wherein the sleeve has a greater stiffness than the stiffness of said elongated flexible ultrasonic probe.

9. A device as defined in claim 1, wherein the elongated flexible ultrasonic probe has a plurality of nodes and anti-nodes along the portion of the length of the probe, and the sleeve has notches or grooves inside the sleeve corresponding to the nodes and anti-nodes so that the motion of the ultrasonic probe is not dampened.

10. A device as defined in claim 1, wherein a first side of the slide-able sleeve is softer than a second side of the slide-able sleeve.

11. A device as defined in claim 10, further comprising a mechanism to adjust the rotation of the slide-able sleeve.

12. A device as defined in claim 1, further comprising a mechanism for the advancement of the sleeve over the elongated flexible ultrasonic probe.

13. A device as defined in claim 1 wherein said elongated flexible ultrasonic probe has a proximal portion and a distal portion, said sleeve being slide-able over the entire distance between said proximal portion and said distal portion.

14. A variable stiffness medical device comprising, an ultrasonic medical device including an elongated flexible ultrasonic probe operating in a transverse mode having a length and an outer surface defining an outer dimension to support a transverse ultrasonic vibration along a portion of the length of the elongated flexible ultrasonic probe, a first sleeve having passage there through, said elongated flexible ultrasonic probe extending through said passage with said outer surface of said elongated flexible ultrasonic probe being engaged by said passage, said sleeve being slide-able along said elongated flexible ultrasonic probe, said first sleeve comprising a thin-walled tube having a substantially constant outer dimension so as to minimize the increase in outer dimension of the elongated flexible ultrasonic probe at the portion thereof upon which the first sleeve is positioned, a second sleeve having a passage there through, said first sleeve extending through said passage in said second sleeve, said first sleeve having an outer surface engaged by said passage in said second sleeve, said second sleeve being slide-able along said first sleeve. second sleeve comprising a thin-walled tube having a substantially constant outer dimension so as to minimize the increase in outer dimension of the elongated flexible ultrasonic probe at the portion thereof upon which the second sleeve is positioned, wherein the variable stiffness medical device provides sufficient residual flexibility to allow for manipulation within an anatomical passage in a human body.

15. A device as defined in claim 14 wherein said first sleeve has length which is approximately one-half the length of said elongated flexible ultrasonic probe, said second sleeve having a length which is approximately one-half the length of said first sleeve.

16. A device as defined in claim 14 wherein said first sleeve is formed of a material of greater stiffness than the stiffness of said elongated flexible ultrasonic probe, said second sleeve being formed of a material of greater stiffness than the stiffness of said first sleeve.

17. A device as defined in claim 14 wherein said second sleeve is being slide-able over the entire length of said first sleeve.

18. A device as defined in claim 14 wherein said first and second sleeves can be used to introduce irrigation fluids and/or remove aspirants from the surgical site.

* * * * *